United States Patent [19]

Bruse et al.

[11] Patent Number: 5,282,798

[45] Date of Patent: Feb. 1, 1994

[54] APPARATUS FOR SUPPORTING AN ORBICULARLY TIPPED SURGICAL LASER FIBER

[75] Inventors: Johnny M. Bruse, Magnolia, Tex.; John P. Novak, Jr., San Jose; John P. Morley, Los Altos, both of Calif.; Gerald D. Abell, Spring, Tex.

[73] Assignees: Heraeus Surgical, Inc., Milpitas, Calif.; Surgical Laser Products, Inc., The Woodlands, Tex.

[21] Appl. No.: 835,196

[22] Filed: Feb. 12, 1992

[51] Int. Cl.⁵ .............................................. A61N 5/06
[52] U.S. Cl. .......................................... 606/17; 606/4; 606/16; 604/167
[58] Field of Search .................. 606/4, 15, 16, 17; 128/395, 397; 604/164, 167

[56] References Cited

U.S. PATENT DOCUMENTS

| | | |
|---|---|---|
| 3,865,113 | 2/1975 | Sharon et al. |
| 4,537,193 | 8/1985 | Tanner ................................ 606/15 |
| 4,538,609 | 9/1985 | Takenaka et al. |
| 4,629,450 | 12/1986 | Suzuki et al. .................... 604/167 |
| 4,671,273 | 7/1987 | Lindsey |
| 4,674,499 | 6/1987 | Pao ..................................... 606/50 |
| 4,693,244 | 9/1987 | Diakuzono |
| 4,950,267 | 8/1990 | Ishibara et al. .................... 606/15 |
| 4,966,587 | 10/1990 | Baumgart ........................... 604/167 |

FOREIGN PATENT DOCUMENTS 9102562 3/1991 PCT Int'l Appl. ............... 606/16

Primary Examiner—Stephen C. Pellegrino
Assistant Examiner—Sonya C. Harris
Attorney, Agent, or Firm—Workman, Nydegger & Jensen

[57] ABSTRACT

The present invention is directed to a new and useful handpiece for use in connection with a orbicularly tipped contact surgical laser. The handpiece has a handle portion and an extended portion. The handle portion is sized for comfortable handling and is of sufficient strength to accommodate the stresses incident to use in rigorous applications such as orthopedic surgery. The extended portion is connected to the handle portion, and is sized so as to be inserted into the surgical site. The extended portion of the handpiece is adapted to enclose and support the orbicular tip of the optical fiber. An introducer which fits snugly to the outside of the extended portion may be utilized to ease the task of placing the contact tip within the surgical site and also to restrict loss of cooling liquids from the insertion incision. The present invention is also directed to an optical fiber assembly for use in contact laser surgery which includes a handpiece of the type described above in combination with a contact optical fiber terminating in an orbicular tip having a diameter larger than the diameter of the optical fiber.

11 Claims, 3 Drawing Sheets

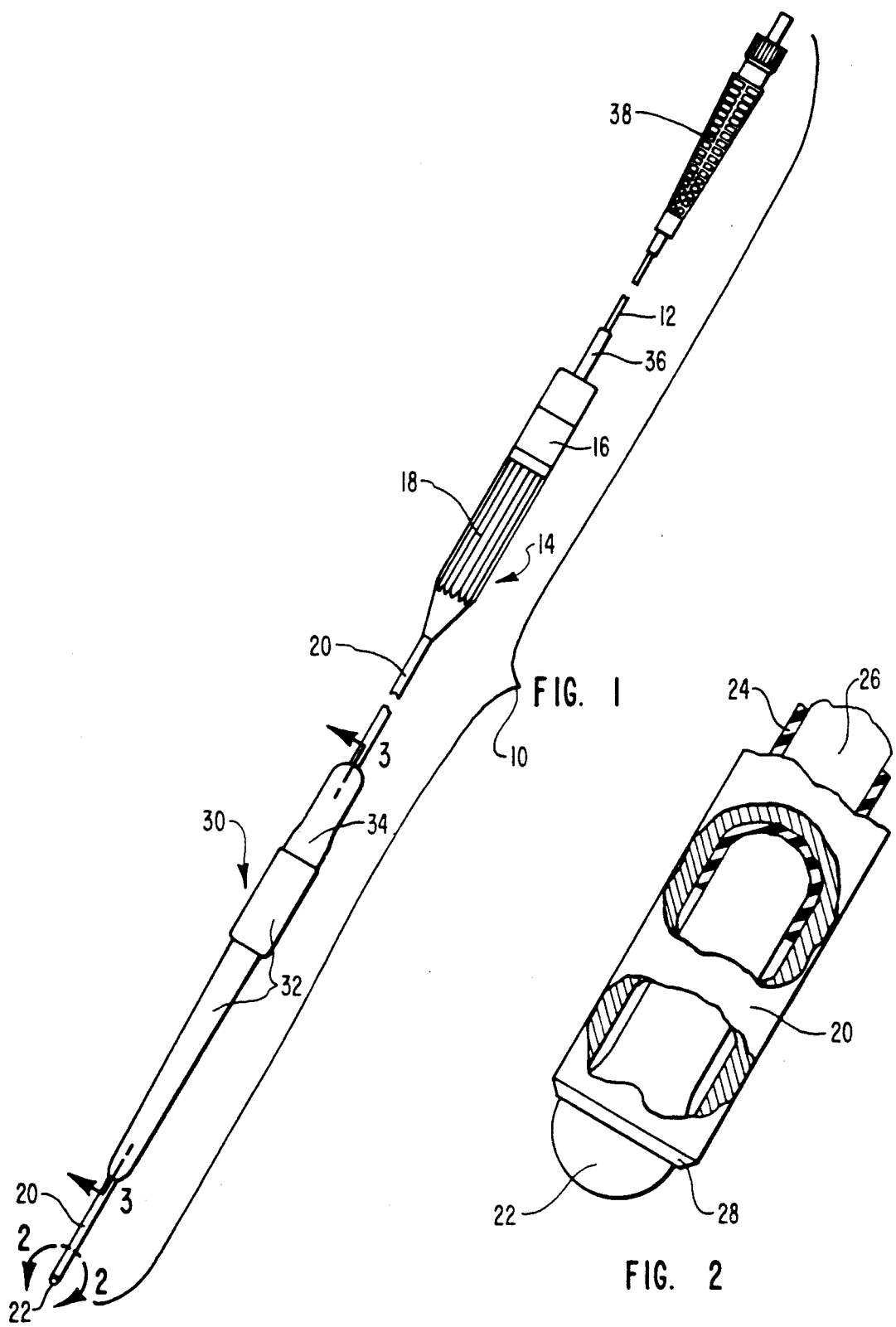

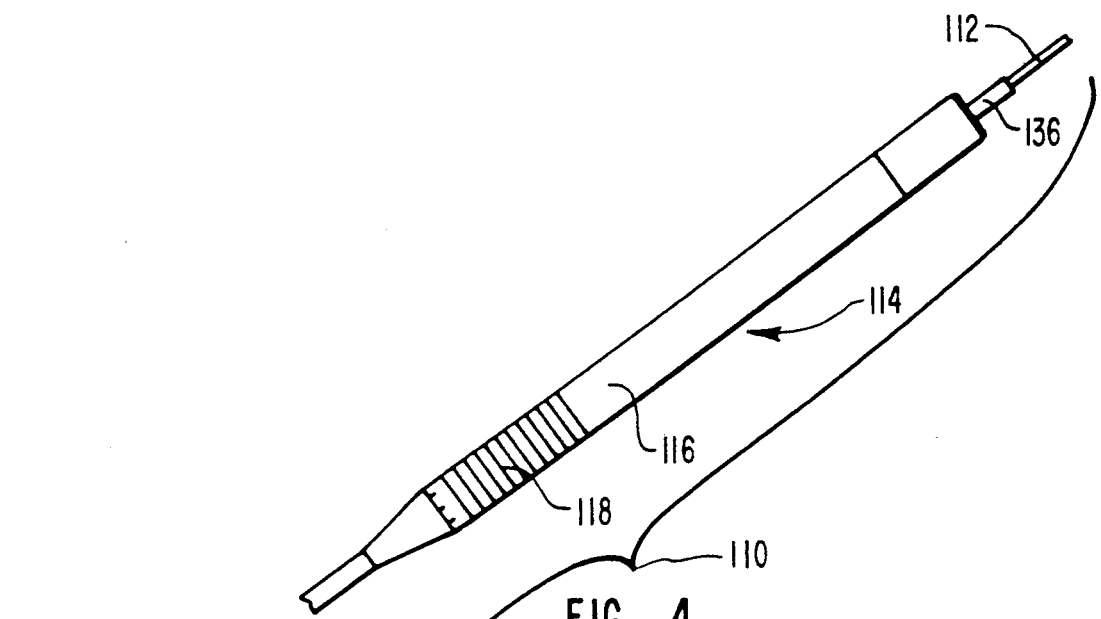
FIG. 4
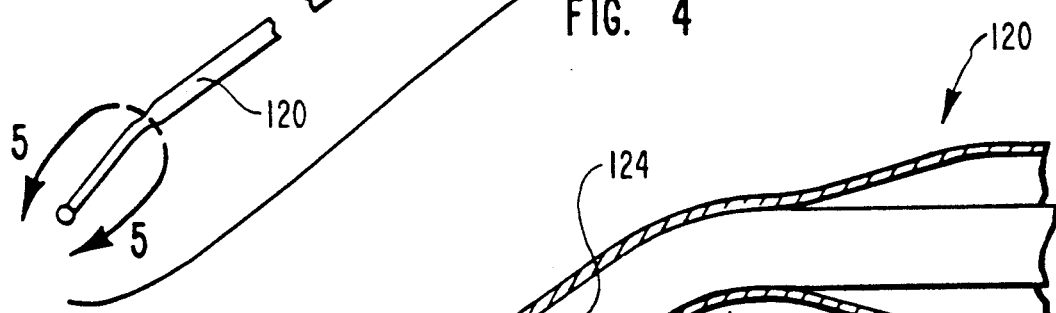
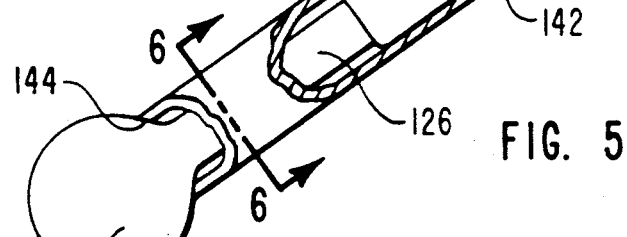
FIG. 5
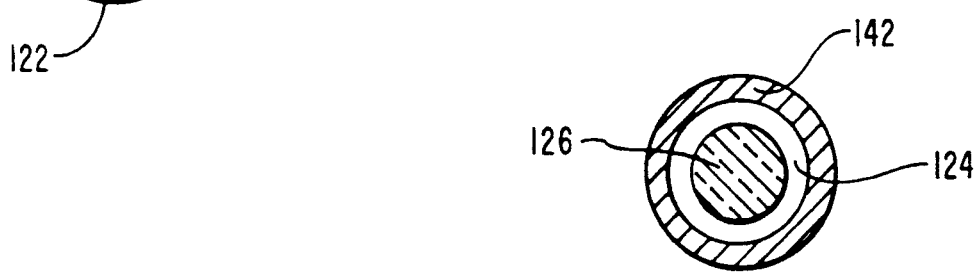
FIG. 6

APPARATUS FOR SUPPORTING AN ORBICULARLY TIPPED SURGICAL LASER FIBER

BACKGROUND OF THE INVENTION

(1.) Technical Field

The present invention relates to surgical lasers, and more particularly to handpieces used in connection with surgical lasers.

(2.) Background Information

Surgical lasers have become as much a part of a typical surgeon's tools as are conventional scalpels. They are useful in a broad range of applications to coagulate, vaporize, excise or anastomose appropriate tissues. A common neodymium yttrium aluminum garnet (Nd:YAG) laser, for example, is widely used to facilitate removal of tissue with very little bleeding.

Conventional surgical lasers involve transmission of laser energy from a laser source through a fiber optic waveguide and out through a lens structure optically coupled to the end of the fiber optic. The lens structure focuses laser energy at a point spaced a short distance from the tip of the lens structure. In use, the lens structure is brought close to target tissue, so as to bring the focused beam to bear upon the tissue.

Fiber optic waveguides are generally sheathed along their length in one or more layers of protective materials in order to protect the fiber from damage and to guard against escape of laser energy except at the tip. A sheathed fiber optic waveguide is generally referred to as a "dressed" fiber. Most fibers used in surgical lasers have a very small diameter, usually in the range of about 400 to 1000 microns. An advantage of fiber optic waveguides is their significant degree of flexibility, making it easy for a physician to manipulate the "cutting" tip without significant impediment from the trailing fiber. Although both flexibility and a small diameter are important to the function of a surgical laser, these properties make it necessary to provide a handpiece to support the fiber optic and thereby give the surgeon a more comfortable and rigid gripping surface.

More recently, developments in laser technology have led to the use of contact tip laser systems in place of traditional noncontact laser systems. A particularly efficient and economical contact tip laser system utilizes a fiber optic provided with a unitary tip in a tapered or spherical (also referred to as "orbicular") shape. Unfortunately, being formed from fiber optic material, unitary contact tips are subject to damage or to breakage when used roughly. This is a problem of particular concern in applications such as orthopedics.

Orthopedic surgery often involves repair of damaged joints. A movable and load-bearing joint, such as the knee, is composed of a relatively complex network of interworking elements in order to accommodate the stresses associated with everyday movements and activities. The ends of the bones in a joint are capped with cartilage and a tough fibrous capsule to reduce friction and to absorb shock. A movable joint is provided with a system of tendons and ligaments to tie everything relatively tightly together. Large joints such as the knee also contain small fluid-filled sacs, called bursas, which act as shock absorbers. The fibrous capsule, tendons, ligaments and bursas are lined with synovial tissue, which excretes synovial fluid to lubricate the moving parts of the joint.

It will be appreciated that a typical joint does not readily accommodate insertion of a surgical laser fiber, even when small diameter fibers are used. Often, the surgeon must exert significant force on the handpiece in order to force the tip of the fiber around the various tendons and ligaments in order to reach, for example, a damaged piece of cartilage at a bone surface. Often, these movements will break the typically spherical contact tip off, leaving it in the patient's joint. A surgeon who performs procedures such as orthopedics is faced with the unpleasant alternatives of either accepting the risk that a contact tip will break off inside the patient, or switching to use of a more expensive and less efficient surgical laser system not utilizing a unitary contact laser tip.

SUMMARY OF THE INVENTION

It is a primary object of the present invention to provide means whereby a surgeon can utilize a unitary contact tip in environments such as found in orthopedics without any significant risk that the tip will break off.

Another object of the present invention is to provide a handpiece capable of accommodating the stresses of rigorous use in applications such as orthopedics.

Additional objects and advantages of the invention are set forth hereinbelow in the detailed description, or will be appreciated by the practice of the invention.

To achieve the foregoing objects, and in accordance with the invention as embodied and broadly described herein, the present invention is directed to a new and useful handpiece for use in connection with a spherically tipped contact surgical laser. The handpiece has a handle portion and an extended portion. The handle portion is sized for comfortable handling and is of sufficient strength to accommodate the stresses incident to use in rigorous applications such as orthopedic surgery. The extended portion is connected to the handle portion, and is sized so as to be inserted along with the optical fiber into the surgical site. The extended portion of the handpiece is adapted to enclose and support the orbicular tip of an orbicularly tipped optical fiber.

An introducer which fits snugly to the outside of the extended portion may be utilized to ease the task of placing the contact tip within the surgical site and also to restrict loss of cooling liquids from the insertion incision.

The present invention is also directed to an optical fiber assembly for use in contact laser surgery which includes a handpiece of the type described above in combination with a contact optical fiber terminating in an orbicular tip having a diameter larger than the diameter of the optical fiber.

BRIEF DESCRIPTION OF THE DRAWINGS

In the accompanying drawings, which represent the best mode presently contemplated for carrying out the present invention:

FIG. 1 is a perspective view illustrating use of one preferred embodiment of a handpiece of the present invention in conjunction with an optical fiber and an optional introducer;

FIG. 2 is an enlarged partially cut-away view taken along lines 2—2 of FIG. 1;

FIG. 4 is a perspective view of another presently preferred embodiment of a handpiece of the present invention shown in conjunction with an optical fiber;

FIG. 5 is a partially cut-away view taken along lines 5—5 of FIG. 4; and

FIG. 6 is an axial cross-sectional view taken along lines 6—6 of FIG. 5.

DETAILED DESCRIPTION OF THE PREFERRED EMBODIMENT

Figure 3:
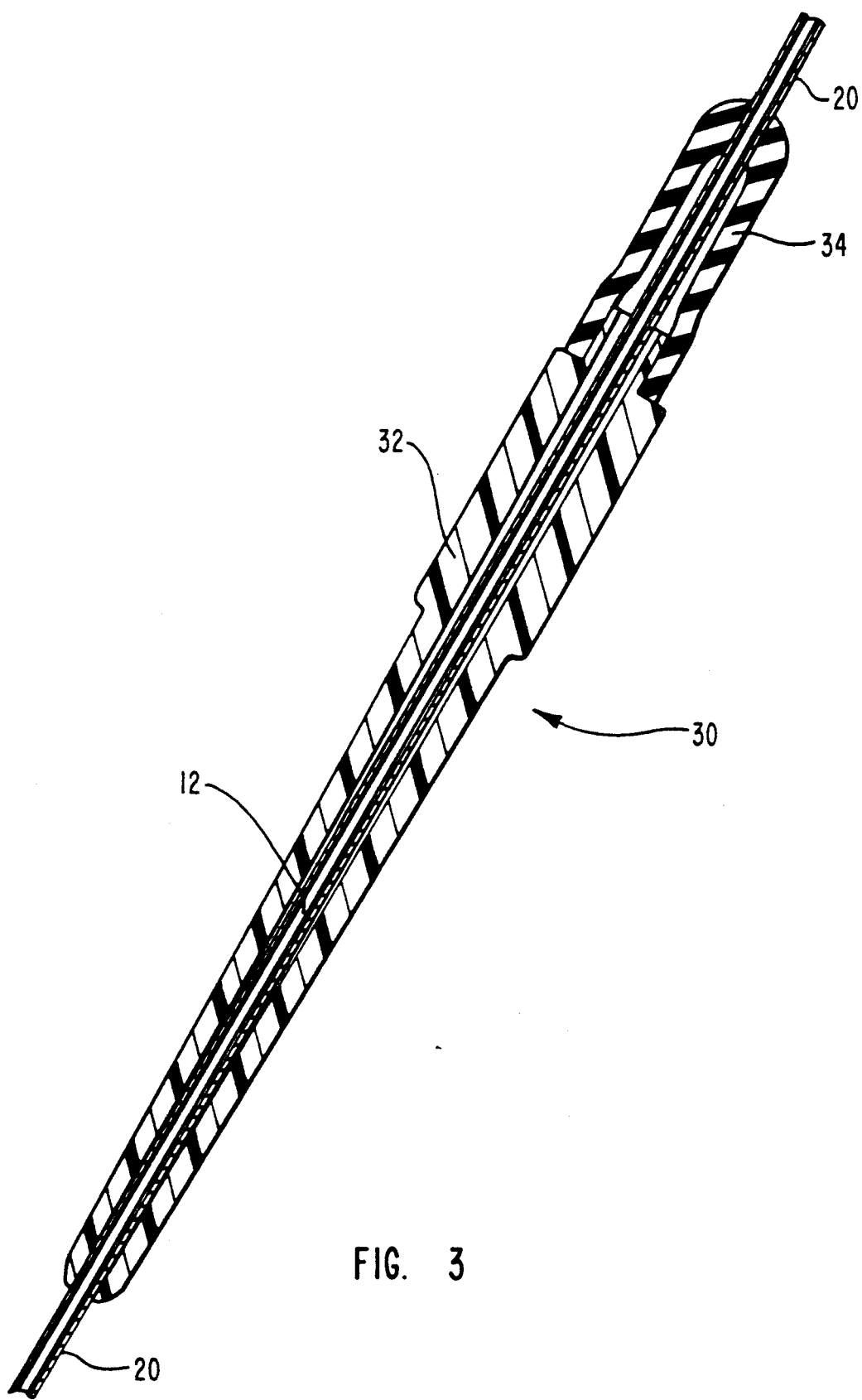
FIG. 3 is a longitudinal cross-sectional view of the introducer, taken along lines 3—3 of FIG. 1.

The present invention is directed to a handpiece for use in connection with a surgical laser optical fiber terminating in an orbicular shaped contact tip, and an assembly of such a handpiece and fiber.

Turning now to the drawings, FIG. 1 depicts one presently preferred embodiment of an optical fiber assembly, shown generally at 10, which includes a dressed optical fiber 12 and a handpiece 14.

Handpiece 14 advantageously has a handle portion 16 having a diameter and a length suitable for comfortable use by a surgeon. A diameter of about 10 millimeters and a length of about 750 millimeters (about 3 inches) has been found adequate for most applications. Handle portion 16 must also be constructed of a material having sufficient strength to withstand the forces imposed by a surgeon's hand during use of the optical fiber assembly 10. The embodiment of FIG. 1 utilizes a handle portion 16 formed from a relatively rigid plastic material. As illustrated in FIG. 1, handle portion 16 is advantageously provided with ridges 18 in order to minimize the possibility of slippage as the surgeon manipulates the optical fiber assembly 10 during a surgical procedure.

Affixed to the distal end of the handle portion 16 is an extended portion 20. Extended portion 20 is preferably formed of a strong and relatively rigid material, such as stainless steel. This construction permits the application of force at the handle portion to be transmitted to the operating tip of the surgical laser. This is very useful not only during operation of the laser, at which time the application of mechanical force can substantially assist the surgeon in completing a surgical procedure, but also is of great value during insertion of the tip of the surgical laser past the various ligaments, tendons, and the like, which frequently overlie a surgical site.

Extended portion 20 can be of any suitable length and diameter. The preferred length of the embodiment of FIG. 1, however, is about 17.78 centimeters (7 inches) for typical orthopedic procedures. The preferred outer diameter of the extended portion is about 2.11 millimeters in the illustrated embodiment, thereby facilitating relatively easy insertion and manipulation of the distal end of the optical fiber assembly within a surgical site. The inner diameter of the extended portion is preferably selected so as to hold the dressed optical fiber 12 within extended portion 20 in a loose friction fit.

As best seen in FIG. 2, the distal tip of optical fiber assembly 10 is preferably formed into a generally spherical shape, sometimes referred to as being "orbicular." Dressing 24 is preferably removed from the distal end portion of dressed optical fiber 12, leaving a short length of fiber 26 exposed. The presently preferred optical fiber 26 has a diameter of 1000 microns, although it will be readily appreciated by one of ordinary skill in the art that larger or smaller fibers could be used without departing from the spirit of the invention disclosed herein. When utilizing a 1000 micron fiber 26, the diameter of the orbicular tip 22 of the embodiment illustrated in FIG. 2 is preferably about 1200 microns.

The proximal portion of orbicular tip 22 in the illustrated embodiment is partially retracted into extended portion 20. This configuration protects the tip from stresses which could break it off from the end of fiber 26. Indeed, the embodiment of FIGS. 1 and 2 is adapted to virtually eliminate any possibility of breaking the orbicular tip off of fiber 26, while leaving the distal portion of orbicular tip 22 unobstructed for use in surgical procedures.

The outside of the distal end of extended portion 20 is preferably chamfered, shown at 28 in FIG. 2. The use of chamfering in the manner illustrated makes easier the insertion of the tip of optical fiber assembly 10 through and around various tissues during placement and manipulation of the assembly.

It is advantageous to support the dressed optical fiber at the location where it enters handpiece 14 in order to minimize any possibility of damaging or breaking the fiber. Use of a collar 36, for example, provides increased support at this juncture. If fitted tightly around the dressed optical fiber, collar 36 can also assist in affixing handpiece 14 to fiber 12, thereby helping maintain the proper orientation of orbicular tip 22 at the end of extended portion 20.

The optical fiber assembly 10 of FIG. 1 is useful in any surgical procedure wherein cutting is to be accomplished at the very tip of the fiber. A suitable connector assembly 38 is used to interconnect the proximal end of the fiber optic 26 to a laser source (not shown). An incision is made at an appropriate location, such as at a knee joint, and the distal tip of the optical fiber assembly of the present invention is inserted through the incision. The tip is then manipulated around the various tendons and ligaments in order to reach, for example, a damaged piece of cartilage at a bone surface which requires repair. Unlike previous designs of contact tip surgical lasers, the present invention permits the surgeon to exercise great control over the placement of the surgical laser tip, and even the application of substantial force, without the risk that the tip will be broken off inside the patient.

During a typical surgical procedure utilizing surgical lasers, a source of liquid is injected into the surgical site under great pressure. The use of this liquid serves two purposes. First, a significant amount of heat energy is generated during operation of the laser. Flushing the surgical site with a continuous flow of liquid serves to cool the surgical site, thereby preventing the temperature from climbing too high, and hence damaging healthy tissue at the surgical site. Second, injecting fluid into the surgical site under pressure serves to separate the overlying skin from underlying bone, muscle, tendons, and the like, thereby making easier the task of manipulating the tip of the surgical laser within the surgical field.

One problem that is presented during the use of pressurized liquid, however, is that the liquid tends to leak out any available opening. The incision through which the end of the optical fiber assembly 10 is inserted is no exception. Significant amounts of liquid will typically escape from the around the extended portion 20 of handpiece 14. Such escape may result in waste of excessive amounts of the cooling liquid, and will also flood the area around the incision unless escaping liquid is continuously sponged up.

An introducer 30 may advantageously be provided that significantly reduces this leakage problem, and also facilitates insertion of the optical fiber assembly through in incision site. Introducer 30 is preferably formed in two parts, a leading portion 32 and a trailing portion 34. In the preferred embodiment shown in FIGS. 1 and 3, leading portion 32 is formed from a semirigid plastic material. It has an inside diameter slightly greater than the extended portion 20 of handpiece 14, thereby permitting easy movement along the length of extended portion 20. Trailing portion 34 is preferably formed from a more elastic material, and is sized so as to fit in a relatively loose friction fit with extended portion 20 so that the introducer will remain in place unless some force is applied, whereupon the introducer will slide along the length of extended portion 20 of the handpiece.

The leading edge of introducer 30 is preferably tapered so as to facilitate insertion thereof through an incision. In use, introducer is advanced to the distal end of the optical fiber assembly, or even slightly past the end. Next, the introducer is pushed through the incision, which should be small enough so that the introducer substantially plugs the incision opening when inserted. Finally, the extended portion is advanced to the incision site, and surgery is commenced. The relatively tight fit between the introducer and the incision on the outside, and the introducer and the extended portion of the handpiece on the inside substantially seals off any significant loss of cooling liquid. In cases where the introducer is unwanted, it is easily removed by simply sliding it off the end of the optical fiber assembly.

Another embodiment of the present invention is illustrated in FIG. 4. This embodiment not only depicts a second presently preferred embodiment of an optical fiber assembly in accordance with the present invention, but also demonstrates several of the types of changes which may be made without departing from the spirit and essential teachings of the invention. It should be understood, however, that other changes might also be made within the scope of the present invention.

FIG. 4 illustrates an optical fiber assembly 110 comprised of an optical fiber 112 and a handpiece 114. Handpiece 114 includes a handle portion 116 and an extended portion 120. Handle portion 116 is preferably provided with ridges 118, and is sized and shaped for comfortable use by a surgeon. The presently preferred material for the handpiece of FIG. 4 is plastic, although it will be appreciated that stainless steel or other materials could be used.

Optionally, as seen best in FIG. 5, extended portion 120 may taper from a larger, and hence stronger, diameter 140 near the handle portion, to a narrower, and hence more easily inserted, diameter 142 near the tip of the optical fiber assembly. A narrow diameter at the tip also facilitates ease of vision at the surgical site. FIG. 6 illustrates the preferred situation wherein dressing 124 fits snugly within the narrower diameter portion 142 of extended portion 120. This construction serves the dual function of assisting to retain the fiber within the handpiece 114, and also supports the working end of the fiber optic. The proximal end of handpiece is preferably provided with a collar 136 to secure handpiece 114 to the dressed optical fiber 112 and to protect optical fiber 112 from damage at the point where it enters the handpiece.

Many surgeons prefer a large orbicular tip over a smaller tip. The embodiment of FIGS. 4-6 utilizes a larger orbicular tip 122 than the tip of FIGS. 1-3. In the preferred embodiment of FIGS. 4-6, fiber optic 126 is 1000 microns in diameter, and the orbicular tip 122 is preferably 2000 microns in diameter, or even larger. Such a large tip is particularly susceptible to breakage, however, and breakage has been a significant problem prior to introduction of the present invention. As best seen in FIG. 5, the possibility of breakage of a large diameter tip 122 is minimized by retracting the tip against the end of extended portion 120 so that the tip is supported. Preferably, the inner diameter of the distal opening of extended portion 120 is chamfered 144 so as to follow the contours of orbicular tip 122. This configuration further supports orbicular tip 122, and serves to center the tip without scoring it.

FIG. 5 also illustrates that it may be advantageous in some circumstances to provide a bend 146 near the end of extended portion 120. Such a bend is useful because force applied by a surgeon manipulating the handle portion 116 is more easily directed away from the axis of handle portion 116. This can provide increased leverage and otherwise facilitate the performance of some types of surgical procedures.

It is to be understood that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Patent is:

1. A handpiece for use with a surgical laser optical fiber which terminates with an orbicular tip, comprising:

a handle portion having a longitudinal axis, said handle portion having an inside diameter sufficient to accept a surgical laser optical fiber, and having an outside diameter suitable for comfortable holding by a surgeon;

an extended portion connected to the handle portion and having a proximal end and a distal end, and said extended portion being comprised of first and second sections having two different diameters, the first section having a proximal end and a distal end and being located at the distal end of the extended portion and having an inner diameter sized to accept a dressed optical fiber while facilitating ease of vision and insertion at an insertion site and the inner diameter at the distal end being chamfered so as to follow the contours of the orbicular tip of the optical fiber, and an outer diameter suitable for insertion into a surgical site, and the second section being located proximal to the first section and having a diameter larger than the outer diameter of the first section so as to provide increased strength, the first and second sections of the extended portion being joined by a tapered section.

2. A handpiece as defined in claim 1, wherein the outer diameter of the first section of the extended portion of the handpiece is chamfered.

3. A handpiece as defined in claim 1, wherein the extended portion is provided with a bend near the proximal end of the first section, so that force applied by a surgeon manipulating the handle portion will be directed partially away from the axis of the handle portion.

4. An optical fiber assembly for use in contact laser surgery, comprising:
   an optical fiber having a diameter and terminating in an orbicular tip having a diameter larger than the diameter of said optical fiber;
   a handpiece for said optical fiber, said handpiece comprising a handle portion having a proximal end and a distal end and a longitudinal axis, and an extended portion having a proximal end and a distal end,
      said handle portion having an outside diameter suitable for comfortable holding by a surgeon and further having a longitudinal axis;
      the proximal end of the extended portion being connected to the distal end of the handle portion, the distal end of the extended portion extending to a point adjacent to the orbicular tip of said optical fiber so as to provide support to said tip, and the distal end of said extended portion having an inner diameter sized to fit snugly about the fiber and chamfered so as to follow the contours of the orbicular tip of the optical fiber, and having an outer diameter suitable for insertion into a surgical site and for providing support to the orbicular tip of said optical fiber.

5. An optical fiber assembly as defined in claim 4, wherein the diameter of the orbicular tip is smaller than the outer diameter of the extended portion of the handpiece.

6. An optical fiber assembly as defined in claim 4, wherein the outer diameter of the distal end of the extended portion of the handpiece is chamfered.

7. An optical fiber assembly as defined in claim 4, wherein the diameter of the orbicular tip is at least as large as the outer diameter of the distal end of the extended portion of the extended portion of the handpiece.

8. An optical fiber assembly as defined in claim 4, wherein the extended portion is provided with a bend, so that force applied by a surgeon manipulating the handle portion will be directed partially away from the axis of the handle portion.

9. An optical fiber assembly as defined in claim 4, wherein the extended portion is comprised of first and second sections having two different diameters, the first and second sections each having a proximal end and a distal end,
   the first section being located at the distal end of the extended portion and having a diameter sized to accept a dressed optical fiber while facilitating ease of vision and insertion at an insertion site, and
   the second section being located proximal to the first section and having a diameter larger than the diameter of the first section so as to provide increased strength,
   and further comprising a tapered section joining the first and second sections of the extended portion.

10. An optical fiber assembly as defined in claim 9, wherein the extended portion is provided with a bend near the proximal end of the first section, so that force applied by a surgeon manipulating the handle portion will be directed partially away from the axis of the handle portion.

11. An optical fiber assembly as defined in claim 4, wherein the extended portion is provided with a bend near the proximal end of the first section, so that force applied by a surgeon manipulating the handle portion will be directed partially away from the axis of the handle portion.

* * * * *

UNITED STATES PATENT AND TRADEMARK OFFICE
CERTIFICATE OF CORRECTION

PATENT NO. : 5,282,798
DATED : February 1, 1994
INVENTOR(S) : JOHNNY M. BRUCE et al.

It is certified that error appears in the above-indentified patent and that said Letters Patent is hereby corrected as shown below:

Title page, column 1, line 2, "Bruse et al." should be
--Bruce et al.--
Title page, column 1, line 6, "Johnny M. Bruse" should be
--Bruce et al.--
Abstract, line 18, after "incision" insert --.--
Column 3, line 48, after "diameter" insert --.--
Column 4, line 64, delete first occurrence of "the"

Column 8, line 2, delete "of the extended portion"

Signed and Sealed this

Fourth Day of October, 1994

*Attest:*

BRUCE LEHMAN

*Attesting Officer*    *Commissioner of Patents and Trademarks*